United States Patent
de Groot

(10) Patent No.: US 9,572,312 B2
(45) Date of Patent: Feb. 21, 2017

(54) WATERMELON VARIETY NUN 7201 WMW

(71) Applicant: Nunhems B.V., AC Nunhem (NL)

(72) Inventor: Erik de Groot, Nonantola (IT)

(73) Assignee: Nunhem B.V., AB Nunhem (NL)

( * ) Notice: Subject to any disclaimer, the term of this patent is extended or adjusted under 35 U.S.C. 154(b) by 98 days.

(21) Appl. No.: 14/590,093

(22) Filed: Jan. 6, 2015

(65) Prior Publication Data
US 2015/0110944 A1   Apr. 23, 2015

(51) Int. Cl.
| | | |
|---|---|---|
| *A01H 5/08* | (2006.01) | |
| *A01H 5/00* | (2006.01) | |
| *A01H 4/00* | (2006.01) | |
| *A01H 1/02* | (2006.01) | |
| *C12N 15/82* | (2006.01) | |
| *C12N 5/04* | (2006.01) | |
| *A01G 1/00* | (2006.01) | |

(52) U.S. Cl.
CPC .............. *A01H 5/08* (2013.01); *A01G 1/001* (2013.01); *A23K 10/30* (2016.05); *A23L 19/00* (2016.08); *A23V 2002/00* (2013.01)

(58) Field of Classification Search
None
See application file for complete search history.

(56) References Cited

U.S. PATENT DOCUMENTS

2006/0168701 A1   7/2006   Zhang et al.

FOREIGN PATENT DOCUMENTS

WO        2014076249 A1     5/2014

OTHER PUBLICATIONS

Buttrose et al, 1978, Ann. Bot. 42:599-608.*
Leskovar et al, Acta Hort. 628, ISHS 2003, pp. 147-151.*
Bang et al, Journal of Horticultural Science, 2004, 76 (6) 885-890.*
Karchi et al, 1981, Hassadeh 61:1284-1285.*
Kano, 2004, J. Hort. Sci. Biotechnol. 79:142-145.*
Strang et al (Triploid Mini-Watermelon Variety Trial , 2004).*
Lee et al (Scientia Horticulturae 127 (2010) 93-105).*
Maynard (Acta Horticulturae 318 (1992) 169-178).*
Strang et al (Triploid Mini-Watermelon Variety Trial, 2004).*
Eigsti, Hort Science, 1971, vol. 6, pp. 1-2.
Compton et al., Use of tissue culture and biotechnology for the genetic improvement of watermelon, Plant Cell, Tissue and Organ Culture, 2004, vol. 77, pp. 231-243.
UPOV, Guidelines for the Conduct of Tests for Distinctness, Uniformity and Stability, TG/142/5 (Geneva, 2013), http:// www.upov. int/ under edocs/tgdocs/en/tg142.pdf.
US Department of Agriculture, Agricultural Marketing Service, Objective Description of Variety, Watermelon (Citrullus lanatus (Thunb.) Matsum. & Nakai), http://www.ams.usda.gov/AMSv1.0/getfile?DocName=STELDEV3003729.
Gama et al., Molecular characterization of watermelon cultivars using microsatellite markers, Horticultura Brasileira, 2013, vol. 31, pp. 522-527.
Zhang et al., Development of Genic Male-sterile Watermelon Lines with Delayed-green Seedling Marker, HORTSCIENCE, 1996, vol. 31(1), pp. 123-126.
Vos et al., AFLP: A new technique for DNA fingerprinting, Nucleic Acid Research, 1995, vol. 23, pp. 4407-4414.
Wijnker et al., Hybrid recreation by reverse breeding in Arabidopsis thaliana, Nature Protocols, 2014, vol. 9, pp. 761-772 DOI: doi:10. 1038/nprot.2014.049.
Kihara, Triploid Watermelons, Proceedings of American Society for Horticultural Science, 1951, vol. 58, pp. 217-230.

* cited by examiner

*Primary Examiner* — Lee A Visone

(57) ABSTRACT

The invention relates to the field of *Citrullus lanatus*, in particular to a new variety of watermelon designated NUN 7201 WMW as well as plants, seeds and watermelon fruits thereof.

13 Claims, No Drawings

WATERMELON VARIETY NUN 7201 WMW

FIELD OF THE INVENTION

The present invention relates to the field of plant breeding and, more specifically, to the development of watermelon variety NUN 7201 WMW, also referred to as "NUN 7201", "NUN 7201 F1", "NUN 7201 hybrid" or "Stellar" and parts thereof and seeds from which the variety can be grown. The invention further relates to vegetative reproductions of NUN 7201, methods for in vitro tissue culture of NUN 7201 explants and also to phenotypic variants of NUN 7201WMW. The invention further relates to methods of producing triploid, seedless watermelon fruits of NUN 7201 or of phenotypic variants of NUN 7201 WMW.

The goal of vegetable breeding is to combine various desirable traits in a single variety/hybrid. Such desirable traits may include greater yield, resistance to insects or pests, tolerance to heat and drought, desired earliness, seedless fruits, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop species which has been subject to such breeding programs and is of particular value is the watermelon. It is a member of the Cucurbitacea family. The genus *Citrullus* originated in Africa. The plant is a large and sprawling annual, grown for its fruit. The fruit of most species of *Citrullus* is often coloured attractively, commonly red. Watermelon can contain black seeds, which are considered undesirable for certain uses.

Many different watermelon cultivars have been produced, and watermelon breeding efforts have been underway in many parts of the world. Some breeding objectives include varying the color, texture and flavor of the fruit, and absence of seeds. Other objectives include disease or pest resistance, optimizing flesh thickness, yield, suitability to various climatic circumstances, solid content (% dry matter), and sugar content.

Watermelon (*Citrullus lanatus*) can occur as a dipoloid, tripoid or tetraploid. Seedless watermelon (*Citrullus lanatus* (Thunb.) Matsum. And Nak.) are produced by using pollen from diploid male parent plants to fertilize flowers of tetraploid maternal parent plants. Pollination of the tetraploid flowers with diploid pollen leads to hybrid F1 seeds which are triploid (Kihara, 1951, Proceedings of American Society for Horticultural Science 58: 217-230; Eigsti 1971, Hort Science 6: 1-2). The triploid hybrid plants grown from these F1 seeds are self-infertile as they produce sterile pollen due to chromosome imbalance. The triploid hybrids, therefore, need to be pollinated by a diploid pollenizer to produce watermelon fruit. Triploid plants are, therefore, interplanted with pollenizer plants for fruit production. The "seedless" fruit produced after pollination on the triploid hybrid plant are not truly seedless, but often contain some undeveloped, small, pale seeds, which are edible.

For optimal fruit set, sufficient viable pollen is required. Plants are generally planted at a ratio of 1 pollenizer per every 2-4 triploid plants. Triploid plants and pollenizers are either planted in separate rows (e.g. 1 row of pollenizer and 2-4 rows of triploids), or interplanted within rows (e.g. planting 1 pollenizer plant in between 2 to 3 triploid plants in the same row), or interplanted in narrow rows between rows of triploids (see US 2006/0168701 Table 2). The fruit produced on the pollenizer plants preferably has a different rind pattern from the fruit on the triploid hybrids, so that these can be easily distinguished.

Although hybrid triploid (seedless) watermelons have been grown in the United States for over 40 years, there is still a need for improved varieties. Consumer demand is high, and the seedless fruit of triploid watermelons are very desired, both for the fresh and the processed market. Many different triploid watermelon varieties exist (see e.g. world wide web at cuke.hort.ncsu.edu/cucurbit/wmelon/wmcultab.html), producing fruits of different sizes and shapes, as well as different fruit quality. Grading of fruits is usually done by fruit weight, to distinguish "mini" watermelons, with weights of less than 6 pounds (2.72 kg), "icebox" watermelons with weights of 8-12 pounds (3.62 kg-5.44 kg) or, according to others, of 6 to 15 pounds (2.72 kg to 6.8 kg) and "picnic" watermelons of above the icebox size, so either above 12 lb (above 5.44 kg) or above 15 pounds (above 6.8 kg).

SUMMARY OF THE INVENTION

In one aspect of the invention, a seed of watermelon variety NUN 7201 WMW is provided, wherein a representative sample of said seed has been deposited under Accession Number NCIMB 42695.

In another aspect the invention provides for a hybrid variety of *Citrullus lanatus* called NUN 7201 WMW. The invention also provides for a plurality of seeds of the new variety, plants produced from growing the seeds of the new variety NUN 7201 WMW, and progeny of any of these. Especially, progeny retaining one or more (or all) of the "distinguishing characteristics" or one or more (or all) of the "essential morphological and physiological characteristics" or essentially all physiological and morphological characteristics of NUN 7201 WMW referred to herein, are encompassed herein as well as methods for producing these.

In one aspect, such progeny have all the physiological and morphological characteristics of watermelon variety NUN 7201 WMW when grown under the same environmental conditions. In another aspect such progeny have all the physiological and morphological characteristics as listed in Table 1 as watermelon variety NUN 7201 WMW when measured under the same environmental conditions (i.e.

evaluated at significance levels of 1%, 5% or 10% significance, which can also be expressed as a p value).

In another aspect a plant of the invention or said progeny plants has/have 1, 2, 3, 4 or more or all of the distinguishing characteristics selected from the group consisting of: 1) an average mature fruit diameter at midsection of 18.65 cm; 2) an average mature fruit weight of 4.32 kg; 3) an average leaf length of 18.0 cm; 4) an average leaf width of 19.2 cm; 5) an average mature fruit rind thickness at blossom end of 7.98 mm; 6) a fruit flesh placental separation of 6.67%; 7) a fruit flesh transverse crack of 0%; 8) a leaf size that is type 3—wider than long; 9) a mature fruit primary skin color that is type 4-dark green (Florida Giant) (e.g. RHS code Grey green N189A) and 10) an average % of soluble solids of juice (center of fruit) that is 10.3. In another aspect a plant of the invention has, in addition to the 1, 2, 3, 4 or more or all of the above-cited distinguishing characteristics, 3, 4, 5, 6, 7, 8, or more, or all of the other (average) characteristics as listed in Table 1.

Further, a watermelon fruit produced on a plant grown from these seeds is provided.

In yet another embodiment of the invention, a plant having one, two or three physiological and/or morphological characteristics which are different from those of NUN 7201 WMW and which otherwise has all the physiological and morphological characteristics of NUN 7201 WMW as listed in Table 1, wherein a representative sample of seed of variety NUN 7201 WMW has been deposited under Accession Number NCIMB 42695, is provided.

Further, a vegetatively propagated plant of variety NUN 7201 WMW, or a part thereof, is provided having all the morphological and physiological characteristics of NUN 7201 WMW when grown under the same environmental conditions.

Also a plant part derived from variety NUN 7201 is provided, wherein said plant part is selected from the group consisting of: fruit, harvested fruit, parts of fruits, leaf, pollen, ovule, cell, part of a leaf, petioles, shoots or parts thereof, stems or parts thereof, vines or parts thereof, roots or parts thereof, cuttings, seeds, hypocotyl, cotyledon, flowers or parts thereof, scion, cion, stock, rootstock and flower. Fruits are particularly important plant parts.

DEFINITIONS

"Watermelon" refers herein to plants of the species *Citrullus lanatus*, and fruits thereof.

"Cultivated watermelon" refers to plants of *Citrullus lanatus* i.e. varieties, breeding lines or cultivars of the species *C. lanatus* as well as crossbreds thereof, or crossbreds with other *Citrullus* species, or even with other Cucurbitacea species, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of *Citrullus* and related species.

The terms "watermelon plant designated NUN 7201", "Stellar", "NUN 7201" "7201 WMW" or "variety designated NUN 7201" are used interchangeably herein and refer to a watermelon plant of variety NUN 7201 WMW, representative seed of which having been deposited under Accession Number NCIMB 42695.

"Tissue culture" refers to a composition comprising isolated cells of the same or a different type or a collection of such cells organized into parts of a plant. Tissue culture of various tissues of watermelon and regeneration of plants therefrom is well known and widely published (see, e.g., Compton et al., *Plant Cell, Tissue and Organ Culture* 77: 231-243, 2004. Similarly, the skilled person is well-aware how to prepare a "cell culture".

"UPOV descriptors" are the plant variety descriptors described for watermelon in the "Guidelines for the Conduct of Tests for Distinctness, Uniformity and Stability, TG/142/5 (Geneva, 2013), as published by UPOV (International Union for the Protection of New Varieties and Plants, available on the world wide web at upov.int) and which can be downloaded from the world wide web at upov.int/ under edocs/tgdocs/en/tg142.pdf and is herein incorporated by reference in its entirety.

"USDA descriptors" are the plant variety descriptors for watermelon (*Citrullus lanatus*) as published by the US Department of Agriculture, Agricultural Marketing Service, Plant Variety Protection Office, Beltsville, Md. 20705 (available on the world wide web at ams.usda.gov) and which can be downloaded from the world wide web at ams.usda.gov/AMSv1.0/getfile?dDocName=STELDEV3003729.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Grüben 8•D-97877 Wertheim, Article-No.: Art62-00008 EAN-Nr.: 4250193402112).

As used herein, the term "plant" includes the whole plant or any parts or derivatives thereof, preferably having the same genetic makeup as the plant from which it is obtained, such as plant organs (e.g. harvested or non-harvested fruits), plant cells, plant protoplasts, plant cell tissue cultures or tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, fruits, flowers, leaves, seeds, clonally propagated plants, roots, stems, vines, root tips, grafts, scions, rootstocks, parts of any of these and the like. Also any developmental stage is included, such as seedlings, cuttings prior or after rooting, mature plants or leaves.

"Harvested plant material" refers herein to plant parts (e.g. fruits detached from the whole plant) which have been collected for further storage and/or further use.

"Harvested seeds" refers to seeds harvested from a line or variety, e.g. produced after self-fertilization or cross-fertilization and collected.

"Internode" refers to a portion of a plant stem or vine between nodes.

"Node" refers to the place on a plant stem or vine where a leaf is attached.

A plant having "all the physiological and morphological characteristics" of a referred-to-plant means a plant having the physiological and morphological characteristics of the referred-to-plant when grown under the same environmental conditions; the referred-to-plant can be a plant from which it was derived, e.g. the progenitor plant, the parent, the recurrent parent, the plant used for tissue- or cell culture, etc.

A plant having "essentially all the physiological and morphological characteristics" of a referred-to-plant means a plant having at least 5 (e.g. 6, 7, 8, 9 or all) of the distinguishing physiological and morphological characteristics (distinguishing characteristics as herein defined) when grown under the same environmental conditions of the referred-to-plant (e.g. a plant from which it was derived such as the progenitor plant, the parent, the recurrent parent, the plant used for tissue- or cell culture, etc.). Alternatively, a plant having "essentially all the physiological and morphological characteristics" of a referred-to-plant means a plant having all the characteristics as listed in Table 1 when grown under the same environmental conditions as a referred-to-plant (e.g. a plant from which it was derived such as the progenitor plant, the parent, the recurrent parent, the plant used for tissue- or cell culture, etc.). In another embodiment, a plant having "essentially all the physiological and morphological characteristics" of a referred-to-plant means a plant having all but 1, 2, 3, 4 or 5 of the characteristics as listed in Table 1 when grown under the same environmental conditions as a referred-to-plant (e.g. a plant from which it was derived such as the progenitor plant, the parent, the recurrent parent, the plant used for tissue- or cell culture, etc.).

For NUN 7201 WMW the distinguishing characteristics are 1) average mature fruit diameter at midsection; 2) average mature fruit weight; 3) average leaf length; 4) average leaf width; 5) average mature fruit rind thickness at blossom end; 6) fruit flesh placental separation; 7) fruit flesh transverse crack; 8) leaf size type; 9) mature fruit primary skin color and 10) average % of soluble solids of juice (at center of fruit).

In certain embodiments the plant of the invention has all the physiological and morphological characteristics, except for certain characteristics mentioned, e.g. the characteristic(s) derived from a converted or introduced gene or trait and/or except for the characteristics which differ.

Similarity between different plants is defined as the number of distinguishing characteristics (or the characteristics as listed in Table 1) that are the same between the two plants that are compared when grown under the same environmental conditions. Characteristics are considered "the same" when the value for a numeric characteristic is evaluated at significance levels of 1%, 5% or 10% significance level, or when a non-numeric characteristic is identical, if the plants are grown under the same conditions.

A plant having one or more "essential physiological and/or morphological characteristics" or one or more "distinguishing characteristics" refers to a plant having (or retaining) one or more of the characteristics mentioned in Table 1 when grown under the same environmental conditions that distinguish NUN 7201 WMW from the most similar varieties (such as variety Deluxe), such as but not limited to average number of fruits per plant, fruit flavor and texture, maturity, average flower diameter or average vine length.

"Distinguishing characteristics" or "distinguishing morphological and/or physiological characteristics" refers herein the characteristics which are distinguishing between NUN 7201 WMW and other watermelon varieties, such as Deluxe, when grown under the same environmental conditions, especially the following characteristics: 1) an average mature fruit diameter at midsection of 18.7 cm; 2) an average mature fruit weight of 4.3 kg; 3) an average leaf length of 18.0 cm; 4) an average leaf width of 19.2 cm; 5) an average mature fruit rind thickness at blossom end of 8.0 mm; 6) fruit flesh placental separation of 6.7%; 7) fruit flesh transverse crack of 0%; 8) a leaf size that is type 3—i.e. wider than long—; 9) mature fruit primary skin color that is type 4—dark green (Florida Giant) e.g. RHS N189A and 10) an average % of soluble solids of juice (center of fruit) that is 10.3. In one aspect, the distinguishing characteristics further include at least one, two, three or more (or all) of the characteristics listed in Table 1. All numerical distinguishing characteristics are statistically significantly different at $p \leq 0.05$.

Thus, a watermelon plant "comprising the distinguishing characteristics of NUN 7201 WMW" refers herein to a watermelon plant which does not differ significantly from NUN 7201 WMW in characteristics 1) to 5) above. In a further aspect the watermelon plant further does not differ significantly from NUN 7201 WMW in one or more, or all characteristics 6) to 10) as mentioned above. In yet a further aspect the watermelon plant further does not differ in at least one, two, three, four, five or six (or all) characteristics selected from the characteristics listed in Table 1. In still another aspect the watermelon plant does not differ in any of the distinguishing characteristics 1) to 10) listed above.

The physiological and/or morphological characteristics mentioned above are commonly evaluated at significance levels of 1%, 5% or 10%, when measured under the same environmental conditions. For example, a progeny plant of NUN 7201 WMW may have one or more (or all) of the essential physiological and/or morphological characteristics of NUN 7201 WMW listed in Table 1, as determined at the 5% significance level (i.e. $p \leq 0.05$) when grown under the same environmental conditions.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A variety is referred to as an "Essentially Derived Variety" (EDV) i.e., shall be deemed to be essentially derived from another variety, "the initial variety" when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcrossing, or transformation by genetic engineering.

"Plant line" is for example a breeding line which can be used to develop one or more varieties. Progeny obtained by selfing a plant line has the same phenotype as its parents.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, vines, fruit, petiole, etc. When a whole plant is regenerated by vegetative propagation, it is also referred to as a vegetative propagation.

"Planting" or "planted" refers to seeding (direct sowing) or transplanting seedlings (plantlets) into a field by machine or hand.

"Interplanting" refers to the combination of two or more types of seeds and/or transplants sown or transplanted (or planted) on the same field, especially the sowing and/or transplanting (or planting) of pollenizers in the same field as triploid hybrid plants (for seedless fruit production on the triploid plants and diploid fruit production on the pollenizer plants). For example, the pollenizer may either be planted in separate rows or interplanted with the triploid plants in the same row (e.g. in hills within each row). Pollenizers may also be planted in between rows of triploids. Also seeds of pollenizers and triploid hybrids may be mixed prior to seeding, resulting in random seeding. The transplants of the triploid hybrid plants and/or pollenizer plants may also comprise a rootstock of a different plant. Suitable rootstocks are known in the art. Watermelon plants with a different rootstock are referred to as "grafted".

"Yield" means the total weight of all watermelon fruits harvested per hectare of a particular line or variety. It is understood that "yield" expressed as weight of all watermelon fruits harvested per hectare can be obtained by multiplying the number of plants per hectare times the "yield per plant".

"Marketable yield" means the total weight of all marketable watermelon fruits, especially seedless triploid fruit of at least 2.5 kg, harvested per hectare of a particular line or variety, i.e. fruits suitable for being sold for fresh consumption, having good flavor (no off-flavors), at least 10% brix (or Total Soluble Solids, TSS, as determined using a refractometer) and flesh color properties and no or very low levels of deficiencies such as hollow heart.

"Selfing" refers to self-pollination of a plant, i.e., the transfer of pollen from the anther to the stigma of the same plant. "Crossing" refers to the mating of two parent plants.

"Average" refers herein to the arithmetic mean.

"Substantially equivalent" refers to a characteristic that, when compared, does not show a statistically significant difference (e.g., p=0.05) from the mean. ANOVA is a suitable method for determining the value of p.

"Locus" (plural loci) refers to the specific location of a gene or DNA sequence on a chromosome. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Maturity" refers to the fruit developmental stage when the fruit has fully developed (reached its final size), begins to ripen and undergoes ripening, during which fruits can be divided into 1, 2, 3 or more maturity stages. Thereafter, fruits become overripe. In particular embodiments "maturity" is defined as the mature stage of fruit development and optimal time for harvest. In one embodiment a "mature" watermelon is defined as having reached the stage of maturity which will insure the proper completion of the normal ripening process. In particular embodiments, fruit should be harvested at a maturity stage i.e. substantially near maximum sweetness and flavor intensity.

"Harvest maturity" is referred to as the stage at which a watermelon fruit is ripe or ready for harvest or the optimal time to harvest the fruit. In one embodiment, harvest maturity is the stage which allows proper completion of the normal ripening.

"Flavor" refers to the sensory impression of a food or other substance, especially a watermelon fruit or fruit part (fruit flesh) and is determined mainly by the chemical senses of taste and smell. Flavor is influenced by texture properties and by volatile and/or non-volatile chemical components (organic acids, lipids, carbohydrates, etc.).

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one watermelon line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to plants derived from a plant designated NUN 7201 WMW. Progeny may be derived by regeneration of cell culture or tissue culture or parts of a plant designated NUN 7201 WMW or selfing of a plant designated NUN 7201 WMW or by producing seeds of a plant designated NUN 7201 WMW. In further embodiments, progeny may also encompass plants derived from crossing of at least one plant designated NUN 7201 WMW with another watermelon plant of the same or another variety or (breeding) line, or wild watermelon plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The terms "gene converted" or "conversion plant" in this context refer to watermelon plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a watermelon variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a watermelon plant by transformation. A plant comprising a transgene stably integrated into its genome is referred to as "transgenic plant".

The term "mean" refers to the arithmetic mean of several measurements. The skilled person understands that the appearance of a plant depends to some extent on the growing conditions of said plant. Thus, the skilled person will know typical growing conditions for watermelons described herein. The mean, if not indicated otherwise within this application, refers to the arithmetic mean of measurements on at least 10 different, randomly selected plants of a variety or line.

"Substantially equivalent" refers to a characteristic that, when compared, does not show a statistically significant difference (e.g., p>0.05) from the mean.

DETAILED DESCRIPTION

The present invention relates to a *Citrullus lanatus* variety, referred to as NUN 7201 WMW, which—when compared to check variety Deluxe—has lower average mature fruit diameter at midsection, lower average mature fruit weight, higher average leaf length, higher average leaf width, higher average mature fruit rind thickness at blossom end, lower fruit flesh placental separation, no fruit flesh transverse crack leaf size type, mature fruit primary skin color and higher average % of soluble solids of juice (center of fruit). Also encompassed by the present invention are progeny plants having all but 1, 2, or 3 of the morphological and/or physiological characteristics of NUN 7201 WMW and methods of producing plants in accordance with the present invention.

A watermelon plant of NUN 7201 WMW differs from the most similar comparison variety Deluxe in one or more characteristics (referred herein to as "distinguishing characteristics" or "distinguishing morphological and/or physiological characteristics" (or essential physiological and/or morphological characteristics) selected from:

1) NUN 7201 WMW has an average mature fruit diameter at midsection that is at least 3%, e.g. at least 4, 5, 6, 7, 8% or even about 8.8% lower than Deluxe;
2) NUN 7201 WMW has average mature fruit weight that is at least 10%, e.g. at least 15, 20, 23, 25, 26% or even about 26.4% lower than Deluxe;
3) NUN 7201 WMW has average leaf length that is at least 10%, e.g. at least 15, 20, 22, 24% or even about 25% higher than Deluxe;
4) NUN 7201 WMW has an average leaf width that is at least 15%, e.g. at least 20, 25, 30, 33% or even about 35% higher than Deluxe;
5) NUN 7201 WMW has an average mature fruit rind thickness at blossom end that is at least 5%, e.g. at least 10, 15, 17, 19% or even about 20% thicker than Deluxe;
6) NUN 7201 WMW has an average fruit flesh placental separation that is at least 20%, e.g. at least 30, 40, 45, 48% or even about 49.9% lower than Deluxe;
7) NUN 7201 WMW has no fruit flesh transverse crack while Deluxe has about 20% transverse crack;
8) NUN 7201 WMW has a leaf size that is type 3-wider than long while Deluxe has type 2 (equal length–width);
9) NUN 7201 WMW has mature fruit primary skin color that is type 4-dark green (Florida Giant) (e.g. RHS N189A) while Deluxe has type 3 (medium green (Sugar Baby)) e.g. RHS 144A; and
10) NUN 7201 WMW has an average % of soluble solids of juice (center of fruit) that is at least 5%, e.g. at least 6, 7, 8, 9, 10% or even about 10.8% higher than Deluxe.

In another embodiment the plant of the invention additionally has a leaf petiole length that is at least 30%, e.g. 40%, 50%, 60%, 65% or even at least 67% larger than the leaf petiole of check variety Deluxe. In still another embodiment the plant of the invention has a leaf petiole of about 13.05, e.g. between 10 and 16 or even between 11 and 15, or 12 and 14.

It is understood that "significant" differences refer to statistically significant differences, when comparing the characteristic between two plant lines or varieties when grown under the same conditions. Preferably at least about 10, 15, 20 or more plants per line or variety are grown under the same conditions (i.e. side by side) and characteristics are measured on at least about 10, 15, 20 or more randomly selected plant or plant parts to obtain averages. Thus, physiological and morphological characteristics or traits are commonly evaluated at a significance level of 1%, 5% or 10%, when measured in plants grown under the same environmental conditions.

Thus, in one aspect, the invention provides seeds of the watermelon variety designated NUN 7201 WMW wherein a representative sample of seeds of said variety was deposited under the Budapest Treaty, with Accession number NCIMB 42695.

Seeds of NUN 7201 WMW are obtainable by crossing the male parent with the female parent and harvesting the seeds produced on the female parent. The resultant NUN 7201 WMW seeds can be grown to produce NUN 7201 WMW plants. In one embodiment a plurality of NUN 7201 WMW seeds are packaged into small and/or large containers (e.g., bags, cartons, cans, etc.). The seeds may be disinfected, primed and/or treated with various compounds, such as seed coatings or crop protection compounds.

Also provided are plants of watermelon variety NUN 7201 WMW, or a fruit or other plant part thereof, produced from seeds, wherein a representative sample of said seeds has been deposited under the Budapest Treaty, with Accession Number NCIMB 42695. Also included is a cell culture or tissue culture produced from such a plant It is understood that such tissue or cell culture comprising cells or protoplasts from the plant of the invention can be obtained from a plant part selected from the group consisting of embryos, meristems, cotyledons, hypocotyl, pollen, leaves, anthers, roots, root tips, pistil, petiole, flower, fruit, seed, stem and stalks. In one embodiment a plant regenerated from such a cell or tissue culture said plant expressing all the morphological and physiological characteristics of NUN 7201 WMW.

In one embodiment the invention provides a watermelon plant regenerated from the tissue or cell culture of NUN 7201 WMW, wherein the plant has all of the physiological and morphological characteristics of NUN 7201 WMW as listed in Table 1 when determined at the 5% significance level. In another embodiment, the invention provides a watermelon plant regenerated from the tissue or cell culture of NUN 7201 WMW, wherein the plant has all of the physiological and morphological characteristics of NUN 7201 WMW when determined at the 5% significance level.

Plants of NUN 7201 WMW can be produced by seeding directly in the ground (e.g., field) or by germinating the seeds in controlled environment conditions (e.g., greenhouses) and then transplanting the seedlings into the field. For example, the seed can be sown into prepared seed beds where they will remain for the entire production of the crop. Alternatively, the watermelon seed may be planted or transplanted in prepared mounds.

In another aspect, the invention provides for a watermelon plant of variety NUN 7201 WMW, a representative sample of seed from said variety has been deposited under the Budapest Treaty, with Accession number NCIMB 42695.

In other aspects, the invention provides for a fruit or parts thereof of watermelon variety NUN 7201 WMW, or a plant part, such as pollen, flowers, shoots or cuttings of variety NUN 7201 WMW or parts thereof.

In one embodiment any plant of the invention comprises at least 3, 4, 5 or more, e.g. 6, 7, 8, 9 or all of the following morphological and/or physiological characteristics (i.e. distinguishing characteristics (average values; measured at harvest or market maturity, as indicated on the USDA Objective description of variety—Watermelon (unless indicated otherwise), when grown under the same environmental conditions):

1) NUN 7201 WMW has an average mature fruit diameter at midsection of about 18.7 cm e.g. between about 15 and about 22 or preferably between about 17 and about 20 or between about 18 and 19.2 cm or even between about 18.5 and 18.8 cm;
2) NUN 7201 WMW has an average mature fruit weight of about 4.3 kg e.g. between about 3.0 and about 5.5 kg or preferably between about 3.5 and about 5.0 or between about 4.0 and 4.5 kg or even between about 4.2 and 4.4 kg;
3) NUN 7201 WMW has an average leaf length of about 18.0 cm e.g. between about 14 and about 22 or preferably between about 16 and about 20 or between about 17 and 19 or even between about 17.5 and 18.5 cm;
4) NUN 7201 WMW has an average leaf width of about 19.2 cm e.g. between about 14 and about 24 cm or preferably between about 16 and about 22 cm or between about 18 and 20 cm or even between about 19.0 and 19.5 cm;
5) NUN 7201 WMW has an average mature fruit rind thickness at blossom end of about 8.0 mm e.g. between about 7.0 mm and about 9.0 mm or preferably between about 7.5 mm and about 8.5 mm or between about 7.8 mm and 8.2 mm or even between about 7.9 mm and 8.0 mm;
6) NUN 7201 WMW has an average fruit flesh placental separation of about 6.7% e.g. between about 5 and about 10% or preferably between about 6.0 and about 8% or between about 6.3 and 7.0% or even between about 6.5 and 6.8%;
7) NUN 7201 WMW has a fruit flesh transverse crack of 0%;
8) NUN 7201 WMW has a leaf size that is type 3—wider than long;
9) NUN 7201 WMW has a mature fruit primary skin color that is type 4—dark green (Florida Giant) e.g. RHS N189A; and
10) NUN 7201 WMW has an average an average % of soluble solids of juice (center of fruit) of about 10.3 e.g. between about 7 and about 13 or preferably between about 8 and about 12 or between about 9 and 11 or even between about 10 and 10.5.

In still another aspect the invention provides a method of producing a watermelon plant, comprising crossing a plant of watermelon variety NUN 7201 WMW with a second watermelon plant one or more times, and selecting progeny from said crossing.

In yet another aspect the invention provides a method of producing a watermelon plant, comprising selfing a plant of watermelon variety NUN 7201 WMW one or more times, and selecting progeny from said selfing.

In other aspects, the invention provides for progeny of variety NUN 7201 WMW such as progeny obtained by further breeding NUN 7201 WMW. Further breeding NUN 7201 WMW includes selfing NUN 7201 WMW one or more times and/or cross-pollinating NUN 7201 WMW with another watermelon plant or variety one or more times. In particular, the invention provides for progeny that retain all the essential morphological and physiological characteristics of NUN 7201 WMW or that retain one or more (e.g. 1) to 5) or 1) to 10) or all) of the distinguishing characteristics of the watermelon type described further above, or, in another embodiment, progeny that retain all morphological and physiological characteristics of NUN 7201 WMW as listed in Table 1; when grown under the same environmental conditions, when determined at the 5% significance level. In another aspect, the invention provides for vegetative reproductions of the variety and plants having all but 1, 2, or 3 of the physiological and morphological characteristics of NUN 7201 WMW (e.g. as listed in Table 1).

The morphological and/or physiological differences between plants according to the invention, i.e. NUN 7201 WMW or progeny thereof, or plants having all but 1, 2, or 3 of the physiological and morphological characteristics of NUN 7201 WMW (as listed in Table 1); and other known varieties can easily be established by growing NUN 7201 WMW next to the other varieties (in the same field, under the same environmental conditions), preferably in several locations which are suitable for said watermelon cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby maturity, ploidy, plant sex form, leaf shape, leaf color, stem shape, surface and length, flower size and color, fruit group, mature fruit color, fruit size, fruit shape, rind texture and thickness, flesh texture and color, disease resistance, insect resistance, can be measured and directly compared for species of *Citrullus lanatus*.

The morphological and physiological characteristics (and distinguishing characteristics) of NUN 7201 WMW, are provided in the Examples, in Table 1. Encompassed herein are also plants derivable from NUN 7201 WMW (e.g. by selfings and/or crossing and/or backcrossing with NUN 7201 WMW and/or progeny thereof) comprising all the physiological and morphological characteristics of NUN 7201 WMW listed in Table 1 as determined at the 5% significance level when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of fruits can be compared, such as cold storage holding quality, post-harvest rind firmness and/or flesh firmness can be measured using known methods.

Flesh firmness can for example be measured using a penetrometer, e.g. by inserting a probe into the fruit flesh and determining the insertion force, or by other methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World wide web at rhs.org.uk/Plants/RHS-Publications/RHS-colour-charts).

In a preferred embodiment, the invention provides for watermelon fruits of variety NUN 7201 WMW, or a part of the fruit. In another embodiment, the invention provides for a container comprising or consisting of a plurality of harvested watermelon fruits of NUN 7201 WMW, or progeny thereof, or a derived variety.

In yet a further embodiment, the invention provides for a method of producing a new watermelon plant. The method comprises crossing a plant of the invention NUN 7201 WMW, or a plant comprising all but 1, 2, or 3 of the morphological and physiological characteristics of NUN 7201 WMW (as listed in Table 1), or a progeny plant thereof, either as male or as female parent, with a second watermelon plant (or a wild relative of watermelon) one or more times, and/or selfing a watermelon plant according to the invention i.e. NUN 7201 WMW, or a progeny plant thereof, one or more times, and selecting progeny from said crossing and/or selfing. The second watermelon plant may for example be a line or variety of the species *Citrullus lanatus*, or other *Citrullus* species or even other Cucurbitacea species.

Progeny are a later generation (of seeds) produced from the first cross of the F1 hybrid with another plant (F2) or with itself (S2), or any further generation produced by crossing and/or selfing (F3, F4, etc.) and/or backcrossing (BC2, BC3, etc.) one or more selected plants of the F2 and/or S2 and/or BC2 generation (or plants of any further generation, e.g. the F3) with another watermelon plant (and/or with a wild relative of watermelon). Progeny may have all the physiological and morphological characteristics of watermelon variety NUN 7201 WMW when grown under the same environmental conditions and/or progeny may have (be selected for having) one or more of the distinguishing characteristics of watermelon of the invention. Using common breeding methods such as backcrossing or recurrent selection, one or more specific characteristics may be introduced into NUN 7201 WMW, to provide or a plant comprising all but 1, 2, or 3 or more of the morphological and physiological characteristics of NUN 7201 WMW (as listed in Table 1).

The invention provides for methods of producing plants which retain all the morphological and physiological characteristics of NUN 7201 WMW. The invention provides also for methods of producing a plant comprising all but 1, 2, or 3 or more of the morphological and physiological characteristics of NUN 7201 WMW (e.g. as listed in Table 1), but which are still genetically closely related to NUN 7201 WMW. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 7201 WMW if its DNA fingerprint is at least 80%, 90%, 95% or 98% identical to the fingerprint of NUN 7201 WMW. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Gama et al., 2013. *Horticultura Brasileira* 31: 522-527). The invention also provides plants and varieties obtained by these methods. Plants may be produced by crossing and/or selfing, or alternatively, a plant may simply be identified and selected amongst NUN 7201 WMW plants, or progeny thereof, e.g. by identifying a variant within NUN 7201 WMW or progeny thereof (e.g. produced by selfing) which variant differs from NUN 7201 WMW in one, two or three of the morphological and/or physiological characteristics (e.g. in one, two or three distinguishing characteristics), e.g. those listed in Table 1 or others. In one embodiment the invention provides a watermelon plant having a Jaccard's Similarity index with NUN 7201 WMW of at least 0.8, e.g. at least 0.85, 0.9, 0.95, 0.98 or even at least 0.99.

By crossing and/or selfing also (one or more) single traits may be introduced into the variety of the invention i.e. NUN 7201 WMW (e.g., using backcrossing breeding schemes), while retaining the remaining morphological and physiological characteristics of NUN 7201 WMW and/or while retaining one or more distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 7201 WMW by breeding with NUN 7201 WMW.

Any pest or disease resistance genes may be introduced into a plant according to the invention, i.e. NUN 7201 WMW, progeny thereof or into a plant comprising all but 1, 2, or 3 or more of the morphological and physiological characteristics of NUN 7201 WMW (e.g. as listed in Table 1). Resistance to one or more of the following diseases is preferably introduced into plants of the invention: Anthracnose, Downy Mildew, Fusarium Wilt, Gummy Stem Blight, Squash Mosaic, Watermelon Mosaic, Powdery Mildew, Cucumber Mosaic, Sunburn and Root Knot. Other resistance genes, against pathogenic viruses, fungi, bacteria, nematodes, insects or other pests may also be introduced.

Thus, invention also provides a method for developing a watermelon plant in a watermelon breeding program, using a watermelon plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 7201 WMW or progeny thereof, or a plant comprising all but 1, 2, or 3 or more of the morphological and physiological characteristics of NUN 7201 WMW (e.g. as listed in Table 1), with a different watermelon plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Zhang et al., HORTSCIENCE 31(1):123-126. 1996). For breeding methods in general see Principles of Plant Genetics and Breeding, 2007, George Acquaah, Blackwell Publishing, ISBN-13: 978-1-4051-3646-4.

The invention thus also provides a method of introducing a single locus conversion, or single trait conversion or introducing a desired trait, into a watermelon plant according to the invention and/or into NUN 7201 WMW comprising:
(a) crossing a watermelon plant of variety NUN 7201 WMW, a representative sample of seed of said variety having been deposited under Accession Number NCIMB 42695, with a second watermelon plant comprising a desired single locus to produce F1 progeny plants;
(b) selecting F1 progeny plants that have the single locus;
(c) crossing the selected progeny plants with a plant of NUN 7201 WMW, to produce backcross progeny plants;
(d) selecting backcross progeny plants that have the single locus and one or more (or all) distinguishing characteristics of watermelon according to the invention and/or all the physiological and morphological characteristics of NUN 7201 WMW to produce selected backcross progeny plants; and
(e) optionally repeating steps (c) and (d) one or more times in succession to produce selected second, third or fourth or higher backcross progeny plants that comprise the single locus and otherwise one or more (or all) the distinguishing characteristics of the watermelons according to the invention and/or comprise all of the physiological and morphological characteristics of NUN 7201 WMW, when grown in the same environmental conditions. The invention further relates to plants obtained by this method.

The above method is provided, wherein the single locus confers a trait, wherein the trait is pest resistance or disease resistance.

In one embodiment the trait is disease resistance and the resistance is conferred to Anthracnose, Downy Mildew, Fusarium Wilt, Gummy Stem Blight, Squash Mosaic, Watermelon Mosaic, Powdery Mildew, Cucumber Mosaic, Sunburn and Root Knot.

The invention also provides a watermelon plant comprising at least a first set of the chromosomes of watermelon variety NUN 7201 WMW, a sample of seed of said variety having been deposited under Accession Number NCIMB 42695; optionally further comprising a single locus conversion, wherein said plant has essentially all of the morphological and physiological characteristics of the plant comprising at least a first set of the chromosomes of watermelon NUN 7201 WMW. In another embodiment, this single locus conversion confers a trait selected from the group consisting of male sterility, herbicide tolerance, insect resistance, pest resistance, disease resistance, environmental stress tolerance, modified carbohydrate metabolism and modified protein metabolism.

In one embodiment, NUN 7201 WMW may also be mutated (by e.g. irradiation, chemical mutagenesis, heat treatment, etc.) and mutated seeds or plants may be selected in order to change one or more characteristics of NUN 7201 WMW. Methods such as TILLING may be applied to watermelon populations in order to identify mutants. Similarly, NUN 7201 WMW may be transformed and regenerated, whereby one or more chimeric genes are introduced into the variety or into a plant comprising all but 1, 2, 3, or more of the morphological and physiological characteristics (e.g. as listed in Table 1). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 7201 WMW, or progeny thereof, by transforming NUN 7201 WMW or progeny thereof with a transgene that confers the desired trait, wherein the transformed plant retains all the phenotypic and/or morphological and/or physiological characteristics of NUN 7201 WMW or the progeny thereof and contains the desired trait.

The invention also provides for progeny of watermelon hybrid (F1) variety NUN 7201 WMW obtained by further breeding with NUN 7201 WMW. In one aspect progeny are F2 progeny obtained by crossing NUN 7201 WMW with another plant or S2 progeny obtained by selfing NUN 7201 WMW. Also encompassed are F3 progeny obtained by selfing the F2 plants. "Further breeding" encompasses traditional breeding (e.g., selfing, crossing, backcrossing), marker assisted breeding, and/or mutation breeding. In one embodiment, the progeny have one or more (or all) of the distinguishing characteristics mentioned further above when grown under the same environmental conditions. In a further embodiment the progeny have all the physiological and morphological characteristics of variety NUN 7201 WMW when grown under the same environmental conditions. In another embodiment the progeny have one, two, or three distinct traits (qualitative or quantitative) introduced into NUN 7201 WMW, while retaining all the other physiological and morphological characteristics of variety NUN 7201 WMW when grown under the same environmental conditions.

The invention also provides a plant having one, two or three physiological and/or morphological characteristics which are different from those of NUN 7201 WMW and which otherwise has all the physiological and morphological characteristics of NUN 7201 WMW, wherein a representative sample of seed of variety NUN 7201 WMW has been deposited under Accession Number NCIMB 42695. In particular plants which differ from NUN 7201 WMW in none, one, two or three of the characteristics mentioned in Table 1 are encompassed.

In one aspect, the plant having one, two or three physiological and/or morphological characteristics which are different from those of NUN 7201 WMW and which otherwise has all the physiological and morphological characteristics of NUN 7201 WMW differs from NUN 7201 WMW in one, two or three of the distinguishing morphological and/or physiological characteristics selected from 1) average mature fruit diameter at midsection; 2) average mature fruit weight; 3) average leaf length; 4) average leaf width and 5) average mature fruit rind thickness at blossom end, 6) fruit flesh placental separation; 7) fruit flesh transverse crack; 8) leaf size type; 9) mature fruit primary skin color and 10) average % of soluble solids of juice (center of fruit).

In another embodiment the plant having one, two or three physiological and/or morphological characteristics which are different from those of NUN 7201 WMW and which otherwise has all the physiological and morphological characteristics of NUN 7201 WMW differs from NUN 7201 WMW in one, two or three morphological or physiological characteristic other than the "distinguishing morphological and/or physiological characteristics" (or essential physiological and/or morphological characteristics) of NUN 7201 WMW selected from: 1) average mature fruit diameter at midsection; 2) average mature fruit weight; 3) average leaf length; 4) average leaf width and 5) average mature fruit rind thickness at blossom end, 6) fruit flesh placental separation; 7) fruit flesh transverse crack; 8) leaf size type; 9) mature fruit primary skin color and 10) average % of soluble solids of juice (center of fruit).

Watermelons according to the invention, such as the variety NUN 7201 WMW, or its progeny, or a plant having all physiological and/or morphological characteristics but one, two or three which are different from those of NUN 7201 WMW, can also be reproduced using vegetative reproduction methods. Therefore, the invention provides for a method of producing plants, or a part thereof, of variety NUN 7201 WMW, comprising vegetative propagation of variety NUN 7201 WMW. Vegetative propagation comprises regenerating a whole plant from a plant part of variety NUN 7201 WMW (or from its progeny or from or a plant having all physiological and/or morphological characteristics but one, two or three, which are different from those of NUN 7201 WMW), such as a cutting, a cell culture or a tissue culture.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets The invention also provides for a vegetatively propagated plant of variety NUN 7201 WMW (or from its progeny or from or a plant having all but one, two or three physiological and/or morphological characteristics which are different from those of NUN 7201 WMW, or a part thereof, having one or more distinguishing characteristics and/or all the morphological and physiological characteristics of NUN 7201 WMW (except for the characteristics differing), when grown under the same environmental conditions.

Parts of NUN 7201 WMW (or of its progeny or of a plant having all physiological and/or morphological characteristics but one, two or three which are different from those of NUN 7201 WMW) encompass any cells, tissues, organs obtainable from the seedlings or plants, such as but not limited to: watermelon fruits or parts thereof, cuttings, hypocotyl, cotyledon, pollen, scion and the like. Such parts can be stored and/or processed further. Encompassed are therefore also food or feed products comprising one or more of such parts, such as canned, chopped, cooked, roasted, preserved, frozen, dried, pickled, or juiced watermelon fruit from NUN 7201 WMW or from progeny thereof, or from a derived variety, such as a plant having all but one, two or three physiological and/or morphological characteristics which are different from those of NUN 7201 WMW.

In one aspect haploid plants and/or double haploid plants of NUN 7201 WMW, or a plant having all but one, two or three physiological and/or morphological characteristics which are different from those of NUN 7201 WMW, or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

Also provided are plant parts derived from variety NUN 7201 WMW (or from its progeny or from a plant having all but one, two or three physiological and/or morphological characteristics which are different from those of NUN 7201 WMW D), or from a vegetatively propagated plant of NUN 7201 WMW (or from its progeny or from a plant having all but one, two or three physiological and/or morphological characteristics which are different from those of NUN 7201 WMW), being selected from the group consisting of: harvested fruits or parts thereof, pollen, cells, leaves or parts thereof, petioles, cotyledons, hypocotyls, shoots or parts thereof, stems or parts thereof, or vines or parts thereof, roots or parts thereof, cuttings, or flowers.

In one embodiment, the invention provides for extracts of a plant described herein and compositions comprising or consisting of such extracts. In a preferred embodiment, the extract consists of or comprises tissue of a plant described herein or is obtained from such tissue.

In still yet another aspect, the invention provides a method of determining the genotype of a plant of the invention comprising detecting in the genome (e.g., a sample of nucleic acids) of the plant at least a first polymorphism. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a watermelon fruit or part thereof and/or an extract from a fruit or another plant part described herein. The food or feed product may be fresh or processed, e.g., dried, grinded, powdered, pickled, chopped, cooked, juiced, preserved, pickled, or powdered canned, steamed, boiled, blanched and/or frozen, etc.

For example, containers such as cans, boxes, crates, bags, cartons, Modified Atmosphere Packagings, films (e.g. biodegradable films), etc. comprising plant parts of plants (fresh and/or processed) described herein are also provided herein.

Marketable watermelon fruits are generally sorted by size and quality after harvest. Alternatively the watermelon fruits can be sorted by Brix or sugar content.

Watermelons may also be grown for use in grafting or inosculation as rootstocks (stocks) or scions (scions). Typically, different types of watermelons are grafted to enhance disease resistance, which is usually conferred by the rootstock, while retaining the horticultural qualities usually conferred by the scion. It is not uncommon for grafting to occur between cultivated watermelon varieties and related *Citrullus* species. Methods of grafting and vegetative propagation are well-known in the art.

So in one aspect the invention relates to a plant comprising a rootstock or scion of NUN 7201 WMW.

Using methods known in the art like "reverse breeding", it is possible to produce parental lines for a hybrid plant such as NUN 7201 WMW; where normally the hybrid is produced from the parental lines. Such methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Nature Protocols Volume: 9, Pages: 761-772 (2014) DOI: doi:10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 7201 WMW) comprising the step of making double haploid cells from haploid cells from the plant of the invention (NUN 7201 WMW) or a seed of that plant; and optionally crossing these parental lines to produce and collect seeds. In another aspect, the invention relates to a combination of parental lines produced by this method. In still another aspect said combination of parental lines can be used to produce a seed or plant of NUN 7201 WMW when these parental lines are crossed. In still another aspect, the invention relates to a combination of parental lines from which a seed or plant having all but one, two or three physiological and/or morphological characteristics of NUN 7201 WMW can be produced; or in another aspect, wherein a seed or plant having the distinguishing characteristics 1)-5) or 1)-10) of NUN 7201 WMW, as herein defined, can be produced when grown under the same environmental conditions. In still another aspect, the invention relates to a combination of parental lines from which a seed or plant having all the characteristics of NUN 7201 WMW as defined in Table 1 can be produced when grown under the same conditions.

All documents (e.g., patent publications) are herein incorporated by reference in their entirety. Cited references:

Acquaah, Principles of Plant Genetics and Breeding, 2007, Blackwell Publishing, ISBN-13: 978-1-4051-3646-4

Kihara, 1951, Proceedings of American Society for Horticultural Science 58: 217-230;

ams.usda.gov/AMSv1.0/getfile?dDocName=STELDEV3003768 on the worldwide web at rhs.org.uk/Plants/RHS-Publications/RHS-colour-charts on the worldwide web at upov.int/edocs/tgdocs/en/tg076.pdf Eigsti 1971, Hort Science 6: 1-2

GAMA RNCS; SANTOS CAF; DIAS RCS; SOUZA FF. 2013. Molecular characterization of watermelon cultivars using microsatellite markers. Horticultura Brasileira 31: 522-527.

Zhang et al., HORTSCIENCE 31(1):123-126. 1996

Compton et al., Plant Cell, Tissue and Organ Culture 77: 231-243, 2004

US 2006/0168701

Principles of Plant Genetics and Breeding, 2007, George Acquaah, Blackwell Publishing, ISBN-13: 978-1-4051-3646-4

WO2014076249

Vos et al. 1995, Nucleic Acid Research 23: 4407-4414

Nature Protocols Volume: 9, Pages: 761-772 (2014) DOI: doi:10.1038/nprot.2014.049

EXAMPLES

Development of NUN 7201 WMW

The hybrid NUN 7201 WMW was developed from a male and female proprietary inbred line of Nunhems. The female and male parents were crossed to produce hybrid (F1) seeds of NUN 7201 WMW. The seeds of NUN 7201 WMW can be grown to produce hybrid plants and parts thereof (e.g. watermelon fruit). The hybrid NUN 7201 WMW can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 7201 WMW is uniform and stable.

DEPOSIT INFORMATION

A total of 2500 seeds of the hybrid variety NUN 7201 WMW were deposited according to the Budapest Treaty by Nunhems B. V. on Nov. 21, 2016, at or at the NCIMB Ltd., Ferguson Building, Craibstone Estate, Bucksburn, Aberdeen AB21 9YA, United Kingdom (NCIMB). The deposit has been assigned or NCIMB 42695. A deposit of NUN 7201 WMW and of the male and female parent line is also maintained at Nunhems B. V. Access to the deposit will be available during the pendency of this application to persons determined by the Director of the U.S. Patent Office to be entitled thereto upon request. Subject to 37 C.F.R. §1.808 (b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

"USDA descriptors" are the plant variety descriptors for watermelon (*Citrullus lanatus* (Thunb) Matsum. & Nakai)—Exhibit C of the U.S. Department of Agriculture, Agricultural Marketing Service, Science and Technology, Plant Variety Protection Office, Beltsville, Md. 20705, which can be downloaded from the world wide web at ams.usda.gov/AMSv1.0/getfile?dDocName=STELDEV3003768 and which is herein incorporated by reference in its entirety.

The most similar variety to NUN 7201 WMW is Deluxe a commercial variety from US Agriseeds. In Table 1 a comparison between NUN 7201 WMW and Deluxe is shown based on a trial in the USA. Trial location: Acampo Calif. USA, (coordinates: 38.192873° N, -121.232637° W). Transplanting date: Jul. 27, 2013, harvesting date Oct. 30, 2013.

Two replications of 50 plants each, from which 15 plants or plant parts were randomly selected to measure characteristics. In Table 1 the USDA descriptors of NUN 7201 WMW (this application) and reference Deluxe (commercial variety) are summarized.

TABLE 1

| USDA descriptor | NUN 7201 WMW | Deluxe |
|---|---|---|
| 1. General Fruit Type | | |
| Fruit type: 1 = Oblong, 2 = Round Large, 3 = Round small (icebox) | 3 | 3 |

TABLE 1-continued

| USDA descriptor | NUN 7201 WMW | Deluxe |
|---|---|---|
| 2. Area of best adaptation | | |
| Region: 1 = Southern U.S., 2 = Northeast/Central U.S., 3 = Southwest U.S., 4 = Most U.S. Areas, 5 = other | 4 Most U.S. Areas | 4 Most U.S. Areas |
| 3. Maturity | | |
| No. of days from emergence to anthesis | NA | NA |
| No. of days from pollination to maturity | NA | NA |
| Days Relative Maturity (as reported in seed catalogs) | NA | NA |
| Maturity category: 1 = early, 2 = medium, 3 = late | 2 | 1-2 |
| 4. Ploidy | | |
| 1 = diploid, 2 = tetraploid, 3 = triploid | 3 | 3 |
| 5. Plant | | |
| Cotyledon shape: 1 = flat, 2 = folded | NA | NA |
| Plant sex form: 1 = monoecious, 2 = andromonoecious | 1 | 1 |
| No. of main stems at crown | 3.1 | 3.2 |
| 6. STEM | | |
| Stem shape (cross section:) 1 = round, 2 = angular | 2 | 2 |
| Diameter (mm) at second node | NA | NA |
| Stem surface: 1 = glabrous, 2 = scabrous, 3 = pubescent, 4 = bristled | 3 | 3 |
| Vine length (cm) (at last harvest) | 321.1 | 287.6 |
| No. of Internodes (at last harvest) | 38.3 | 38.6 |
| Ratio Vine length (cm): No of internodes (at last harvest) | 8.4 | 7.5 |
| 7. LEAF | | |
| Leaf shape: 1 = ovate, 2 = obovate, 3 = round | 1 | 1 |
| Leaf lobes: 1 = none, 2 = lobed | 2 | 2 |
| Leaf length (cm) | 18.0 | 14.4 |
| Leaf width (cm) | 19.2 | 14.2 |
| Leaf size: 1 = longer than wide, 2 = length-width equal, 3 = wider than long | 3 | 2 |
| Dorsal surface pubescence: 1 = smooth, 2 = pubescent | 2 | 2 |
| Ventral surface pubescence: 1 = smooth, 2 = pubescent | 2 | 2 |
| Leaf color: 1 = light green, 2 = gray green, 3 = medium green, 4 = dark green | 3 | 3 |
| Color chart value (RHS): | Yellow Green 147B | Yellow Green 147B |
| 8. FLOWER | | |
| Diameter across Staminate (cm) | 3.65 | 3.89 |
| Diameter across Pistillate (cm) | 3.85 | 4.04 |
| Flower color: 1 = lemon, 2 = yellow, 3 = orange | 2 | 2 |
| Color chart value (RHS) | Yellow Group 2B | Yellow Group 2B |
| 9. MATURE FRUIT | | |
| Fruit shape: 1 = round, 2 = oval, 3 = cylindrical | 1 | 1-2 |
| Long (cm) | 19.6 | 22.4 |
| Diameter at midsection (cm) | 18.7 | 20.4 |
| Average weight (kg) | 4.3 | 5.9 |
| Maximum fruit weight (kg) | 5.9 | 7.3 |
| Index = length ÷ diameter × 10 | 10.5 | 11.0 |
| Fruit surface: 1 = smooth, 2 = slightly grooved, 3 = deeply grooved | 1 | 1 |
| Skin color pattern: 1 = solid (one color), 2 = stripe, 3 = mottle/net | 2 | 2 |
| Primary color: 1 = Yellow Green (Desert King), 2 = Light Green (Charleston Gray), 3 = Medium Green (Sugar baby), 4 = dark green (Florida Giant) | 4 | 3 |
| Color chart value (RHS chart) | N189A | 144A |
| Secondary color 1 = Yellow Green, 2 = Light Green, 3 = Medium green, 4 = dark green | 4 | 4 |
| Color chart value (RHS chart) | 139A | 139A |
| 10. RIND | | |
| Rind texture: 1 = tender, 2 = brittle, 3 = tough | 3 | 3 |
| Thickness blossom end (mm) | 8.0 | 6.7 |
| Thickness sides (mm) | 9.1 | 10.1 |
| 11. FLESH | | |
| Flesh texture: 1 = crisp, 2 = soft | 1 | 1 |
| Flesh coarseness: 1 = course fibrous, 2 = fine-little fiber | 2 | 2 |
| Flesh color: 1 = white, 2 = yellow, 3 = orange, 4 = pink, 5 = red, 6 = dark red | 5 | 5 |

TABLE 1-continued

| USDA descriptor | NUN 7201 WMW | Deluxe |
|---|---|---|
| Color chart value (RHS chart) | 44D | 35B |
| Refractometer: % Soluble solids of juice (Center of fruit) | 10.3 | 9.3 |
| % Hollow heart | 0 | 0 |
| % Placental separation | 6.7 | 13.3 |
| % Transverse crack | 0 | 20 |

These are typical values. Values may vary due to environment. Other values that are substantially equivalent are also within the scope of the invention. N.A.=not applicable; n.r.=not recorded.

The invention claimed is:

1. A plant, plant part or seed of watermelon variety NUN 7201 WMW, wherein a representative sample of said seed has been deposited under Accession Number NCIMB 42695.

2. A plant or part thereof grown from the seed of claim 1.

3. The plant part of claim 2, further defined as a leaf, pollen, an ovule, a fruit, a scion, a rootstock, cutting, flower or a part of any of these or a cell.

4. A tissue or cell culture of regenerable cells of the plant of claim 2.

5. The tissue or cell culture according to claim 4, comprising cells or protoplasts from a plant part selected from the group consisting of embryos, meristems, cotyledons, hypocotyl, pollen, leaves, anthers, roots, root tips, pistil, petiole, flower, fruit, seed, stem and stalks.

6. A watermelon plant regenerated from the tissue or cell culture of claim 4, wherein the plant has all of the physiological and morphological characteristics of watermelon variety NUN 7201 WMW when grown under the same environmental conditions and determined at the 5% significance level, wherein a representative sample of seed of said variety has been deposited under Accession Number NCIMB 42695.

7. A method of producing of the plant of claim 2, or a part thereof, comprising, a step of vegetative propagation of the plant of claim 2.

8. The method of claim 7, wherein said vegetative propagation comprises a step of regenerating a whole plant from a part of the plant of watermelon variety NUN 7201 WMW, wherein a representative sample of seed of said variety has been deposited under Accession Number NCIMB 42695.

9. The method of claim 7, wherein said part is a cutting, a cell culture or a tissue culture.

10. A vegetative propagated plant of claim 2, or a part thereof, wherein the plant has all of the physiological and morphological characteristics of watermelon variety NUN 7201 WMW when grown under the same environmental conditions, wherein a representative sample of seed of said variety has been deposited under Accession Number NCIMB 42695.

11. A food or feed product comprising the plant part of claim 3.

12. A plant of watermelon variety NUN 7201 WMW further comprising a single locus conversion, wherein a representative sample of seed of said variety has been deposited under Accession Number NCIMB 42695, optionally wherein the single locus conversion confers a trait selected from the group consisting of male sterility, herbicide tolerance, insect resistance, pest resistance, disease resistance, environmental stress tolerance, modified carbohydrate metabolism and modified protein metabolism.

13. A plant comprising the scion or rootstock of claim 3.

* * * * *